United States Patent [19]

Fujii et al.

[11] Patent Number: 5,154,733
[45] Date of Patent: Oct. 13, 1992

[54] PHOTOELECTRON EMITTING MEMBER AND METHOD OF ELECTRICALLY CHARGING FINE PARTICLES WITH PHOTOELECTRONS

[75] Inventors: Toshiaki Fujii, Kanagawa; Kazuhiko Sakamoto, Saitama, both of Japan

[73] Assignee: Ebara Research Co., Ltd., Fujisawa, Japan

[21] Appl. No.: 664,853

[22] Filed: Mar. 5, 1991

[30] Foreign Application Priority Data

Mar. 6, 1990 [JP] Japan .................................. 2-52688
Nov. 2, 1990 [JP] Japan .................................. 2-295423

[51] Int. Cl.$^5$ .............................................. B03C 3/40
[52] U.S. Cl. .......................................... 55/2; 55/102; 55/279; 73/28.02; 209/129; 250/423 P; 422/24
[58] Field of Search ........................ 55/2, 6, 102, 279; 73/28.02, 28.04, 865.5; 422/24, 121; 250/423 P; 15/1.51; 209/3, 129, 571

[56] References Cited

U.S. PATENT DOCUMENTS

| | | | |
|---|---|---|---|
| 2,085,349 | 6/1937 | Wintermute | 55/6 |
| 2,593,377 | 4/1952 | Wintermute | 55/6 |
| 3,403,252 | 9/1968 | Nagy | 55/102 X |
| 3,653,185 | 4/1972 | Scott et al. | 55/102 X |
| 3,846,072 | 11/1974 | Patterson | 422/121 |
| 4,227,446 | 10/1980 | Sone et al. | 55/102 X |
| 4,750,917 | 6/1988 | Fujii | 55/6 |
| 5,060,805 | 10/1991 | Fujii et al. | 55/2 X |

FOREIGN PATENT DOCUMENTS

| | | |
|---|---|---|
| 0404093 | 12/1990 | European Pat. Off. |
| 2376510 | 12/1977 | France |
| 61-178050 | 8/1986 | Japan |
| 62-242838 | 10/1987 | Japan |
| 62-244459 | 10/1987 | Japan |
| 63-54959 | 3/1988 | Japan |
| 63-77557 | 4/1988 | Japan |
| 63-78471 | 4/1988 | Japan |
| 63-84656 | 4/1988 | Japan |
| 63-97247 | 4/1988 | Japan |
| 63-100955 | 5/1988 | Japan |
| 63-100956 | 5/1988 | Japan |
| 63-147565 | 6/1988 | Japan |
| 63-147566 | 6/1988 | Japan |
| 1-262953 | 10/1989 | Japan |
| 1-262954 | 10/1989 | Japan |
| 1-266864 | 10/1989 | Japan |
| 2-8638 | 1/1990 | Japan |
| 2-8639 | 1/1990 | Japan |
| 2-10034 | 1/1990 | Japan |
| 2-10035 | 1/1990 | Japan |
| 2-47536 | 2/1990 | Japan |

OTHER PUBLICATIONS

"Charging of Aerosol Particles by Photoelectric Effect", Aug. 1988, pp. 13-15, The Sixth Technical and Research Forum of Aerosol Science.

K. Sakamoto, et al., "Charging of Aerosol Particles by Use of UV Irradiation", Sep. 1989, pp. 735-740, Man and his Ecosystem: Proceedings of the 8th World Clean Air Congress.

Shinozuka, et al., "Charging and Electrostatic Precipitation of Fine Particles by UV Irradiation", 1989, pp. 63-71, *Environmental Pollution*, vol. 24, No. 5.

*Primary Examiner*—Richard L. Chiesa
*Attorney, Agent, or Firm*—Oblon, Spivak, McClelland, Maier & Neustadt

[57] ABSTRACT

A photoelectron emitting member and method of electrically charging fine particles with photoelectrons, wherein the member includes a matrix that is at least composed of a material capable of transmitting ultraviolet rays and a material that is provided on the surface of the matrix or in its neighborhood and which emits photoelectrons upon irradiation with ultraviolet rays or sunlight. The member emitting photoelectrons upon irradiation with ultraviolet rays or sunlight is disposed in an electric field from the side opposite to the irradiated side. The member permits efficient utilization of the energy of ultraviolet rays. When sunlight is applied to the member to have it emit photoelectrons, particles can be electrically charged with energy costs being reduced to substantially zero.

15 Claims, 3 Drawing Sheets

PHOTOELECTRON EMITTING MEMBER AND METHOD OF ELECTRICALLY CHARGING FINE PARTICLES WITH PHOTOELECTRONS

BACKGROUND OF THE INVENTION

1. Field of the Invention

The present invention relates to a photoelectron emitting member having a photoelectric effect, as well as a method of electrically charging fine particles using that member.

Fine particles electrically charged with photoelectrons have various applications such as (a) separating and classifying fine particles, as well as modifying the surfaces thereof and controlling charge amounts;

(b) measuring the concentration and size of fine particles in gases such as air and waste gases or in a space by using electrically charged fine particles; and (c) trapping and removing charged fine particles to produce clean gases or clean spaces.

1. Prior Art

The present inventor has previously proposed many methods of electrically charging fine particles with photoelectrons that are emitted upon applying uv rays and/or other forms of radiation to a photoelectron emitting member and various applications of the thus formed photoelectron emitting member. In the method of producing clean gases proposed by the present inventor, the following are particularly relevant to the present invention:

(1) Japanese Patent Public Disclosure (Laid-Open) No. 178050/1986 (corresponding to U.S. Pat. No. 4,750,917);

(2) Japanese Patent Public Disclosure (Laid-Open) No. 24459/1987;

(3) Japanese Patent Public Disclosure (Laid-open) No. 77557/1988;

(4) Japanese Patent Public Disclosure (Laid-Open) No. 100955/1988; and (5) Japanese Patent Public Disclosure (Laid-Open) No. 262954/1989.

With regard to the measurements, the following were proposed by the inventor:

(1) Japanese Patent Public Disclosure (Laid-Open) No. 242838/1987;

(2) Japanese Patent Public Disclosure (Laid-Open) No. 47536/1990; and (3) Japanese Patent Application No. 134781/1989.

With regard to the separation and classification, the following was proposed by the inventor: Japanese Patent Application No. 177198/1989 (not yet Laid-Open).

Further, with regard to the conditions of electrically charging fine particles, the following were proposed by the inventor: (1) Japanese Patent Application No. 120563/1989 (not yet Laid-Open) and (2) Japanese Patent Application No. 120564/1989 (not yet Laid-Open).

Furthermore, with regard to photoelectron emitting members, the following were proposed by the inventor: (1) Japanese Patent Application No. 155857/1989 (not yet Laid-Open) and (2) Japanese Patent Application No. 153335/1990 (not yet Laid-Open).

Conventional photoelectron emitting members are made of either single materials in bulk (mass) form or bulk materials having a protective film or a thin-film material provided on their surface. These members emit photoelectrons in a direction opposite to the direction of incidence of ultraviolet rays with which they are irradiated (in other words, photoelectrons are emitted as if they were reflected from the surface of those members). However, the use of these prior art photoelectron emitting members is limited and accordingly, there has been a room for improvement depending on the field of applications and the type of apparatus in which they are used. The problems are briefly described below with reference to an example.

FIG. 3 is a cross section of a conventional air cleaner, which comprises an ultraviolet lamp 1, an ultraviolet radiation transmitting window 2, a photoelectron emitting member 3, electrodes 4 for establishing an electric field, and a charged fine particle trapping plate 5. When air 6 containing fine particles is admitted into the air cleaner, the fine particles in the air are electrically charged with photoelectrons 7 emitted from the member 3 upon irradiation with ultraviolet rays and are trapped by the member 5, whereby clean air is produced at an outlet 8. In the air cleaner shown in FIG. 3, the photoelectron emitting member is provided on the other side of the apparatus which is remote from the uv lamp, so the dose of uv radiation applied to the surface of the photoelectron emitting member is significantly reduced, which is not desirable from the viewpoint of efficient energy use. Further, the apparatus of FIG. 3 does not have a high degree of design flexibility.

SUMMARY OF THE INVENTION

It is an object of the present invention to provide a photoelectron emitting member that permits efficient utilization of the energy of ultraviolet rays.

Another object of the present invention is to provide a method by which fine particles can be electrically charged in an effective way.

Another object of the present invention is to provide a method that is capable of cleaning gases without requiring the application of a high voltage, that is quiet, that is safe and that permits easy maintenance.

Other objects and advantages of the present invention will become apparent to those skilled in the art from the following description and drawings.

DETAILED DESCRIPTION OF THE PREFERRED EMBODIMENTS

The first object of the present invention can be attained by a photoelectron emitting member comprising a matrix that is composed of a material capable of transmitting ultraviolet rays and a material that is provided on the surface of said matrix or in its neighborhood and which emits photoelectrons upon irradiation with ultraviolet rays, said member emitting photoelectrons upon irradiation with ultraviolet rays in an electric field from the side opposite to the irradiated side.

The other objects of the present invention can be attained by a method of electrically charging fine particles with photoelectrons that are generated by irradiating the above-described photoelectron emitting member with ultraviolet rays or sunlight.

The present invention is described below in detail.

Figure 1:
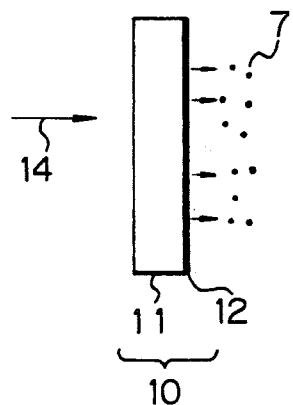
FIG. 1 is a sketch showing the structure and operation of the photoelectron emitting member of the present invention.

FIG. 1 is a sketch showing the structure and operation of the photoelectron emitting member according to the first aspect of the present invention. As shown, the photoelectron emitting member generally indicated by numeral 10 comprises a matrix 11 made of a material that transmits ultraviolet rays and a material 12 that is provided on the surface of said matrix or in its neighborhood and which emits photoelectrons upon irradiation with ultraviolet rays or sunlight. Since the material 12 is provided on the side of the matrix which is opposite the side where an ultraviolet or sunlight radiation 14 is applied, it emits photoelectrons 7 from the remote side of the matrix.

The individual components of the photoelectron emitting member are described below. The ultraviolet transmitting material 11 may be any material that transmits ultraviolet rays and that can be provided on its surface or in its neighborhood with a material that emits photoelectrons upon irradiation with uv rays or sunlight.

Glass material (e.g. synthetic quartz, sapphire glass, uv transmissive glass and borosilicate glass), polymeric materials (e.g. acrylic resins) and $MgF_2$ are typically used, and among them, glass materials are preferred from the viewpoints of performance (effect) and cost. The material 12 which emits photoelectrons upon irradiation with ultraviolet rays may be any material that emits photoelectrons upon exposure to uv rays, and those material which have a smaller photoelectric work function are preferred. From the viewpoints of efficiency and economy, the material 12 is preferably either one of Ba, Sr, Ca, Y, Gd, La, Ce, Nd, Th, Pr, Be, Zr, Fe, Ni, Zn, Cu, Ag, Pt, Cd, Pb, Al, C, Mg, Au, In, Bi, Nb, Si, Ta, Ti, U, B, Eu, Sn and P, or compounds or alloys therof. These materials may be used either on their own or as admixtures. Composites of these material are also usable and an example is a physical composite such as amalgam.

Compounds that can be used as material 12 are oxides, bromides and carbides. Exemplary oxides include BaO, SrO, CaO, $Y_2O_6$, $Gd_2O_3$, $Nd_2O_3$, $ThO_2$, $ZrO_2$, $Fe_2O_3$, ZnO, CuO, $Ag_2O$, $La_2O_3$, PtO, PbO, $Al_2O_3$, MgO, $In_2O_3$, BiO, NbO, and BeO; exemplary borides include $YB_6$, $GdB_6$, $LaB_6$, $NdB_5$, $CeB_6$, $EuB_6$, $PrB_6$ and $ZrB_2$; exemplary carbides include UC, ZrC, TaC, TiC, BnC and WC; and exemplary nitrides include TiN.

Alloys that can be used as material 12 are brass, bronze, phosphor bronze, alloys of Ag and Mg (2-20 wt % Mg), alloys of Cu and Be (1-10 wt % BE) and alloys of Ba and Al. Alloys of Ag-Mg, Cu-Be and Ba-Al systems are preferred.

These materials are provided on the surface of the ultraviolet transmissive material 11 or in its neighborhood. They can be provided by any method as long as they emit photoelectrons upon irradiation with uv rays. Examples of the methods that can be employed include: being coated onto a glass substrate; being embedded in an area near the surface of the substrate; being provided on the substrate which is then coated with another material; and mixing the uv transmissive material with a material which emits photoelectrons. The material 12 may be provided as a thin film, a screen or in lines, strips or other forms. From the view-point of effectiveness, the material 12 is preferably coated or deposited on the surface of the matrix as a thin film by a suitable method such as ion plating, sputtering, evaporation or CVD. The thin film may have a thickness that permits the emission of photoelectrons upon irradiation with ultraviolet rays or sunlight and that ranges from about 5 to about 5,000 Å, typically from about 20 to about 500 Å, preferably about 20 to about 200 Å.

The material 12 described above may be used in various shapes including a flat plate, a pleated plate, a grid and a screen, with the surface being optionally roughened to provide asperities. Projections on the surface may have pointed or spherical tips.

The provision of a thin film on the matrix can be accomplished by the method already proposed by the present inventor and which comprises using one or more materials in either a single or multilayered arrangement. In the latter case, a plurality of thin films are superposed to form a duplex structure of a multiplex structure composed of more than two layers.

An optimum shape of the structure, as well as the kind of the material which emits photoelectrons upon irradiation with uv rays or sunlight, the method of its provision on the matrix and the thickness of its thin film can be determined from the results of preliminary testing in consideration of such factors as equipment need, type of size and configuration of the type of photoelectron emitting member, the strength of an electric field (to be described hereinafter), the manner in which an electric field is applied, operational efficiency and economy.

As described above, the photoelectron emitting material according to the first aspect of the present invention comprises the uv transmissive material (matrix) and the material that is provided on the surface of the matrix or in its neighborhood and that emits photoelectrons upon irradiation with uv rays or sunlight. When uv rays or sunlight are applied to the side of the matrix which is opposite to the side where the photoelectron emitting material is provided, photoelectrons are emitted from the remote side of the matrix to electrically charge fine particles.

The thickness of the matrix can be appropriately determined in line with the specific field of application and from the viewpoint of materials strength and ease of handling. The matrix generally has a thickness of about 0.5-40 mm, preferably about 1-10 mm.

The emission of uv rays is now described below. Any source of uv rays may be used as long as the photoelectron emitting member will emit photoelectrons upon irradiation with uv rays, and exemplary sources are a mercury lamp, a hydrogen discharge tube, a xenon discharge tube, a Lyman discharge tube, sunlight, etc.

The choice of a suitable uv source depends on such factors as the shape of a charging section used, the area of its application, the required precision of measurement, and economy. For example, in biological areas where a microbicidal (sterilizing) action is advantageously provided by uv radiation sources, germicidal lamps (emitting far ultraviolet rays) with a dominant wavelength of 253.7 nm are preferably used as uv radiation sources.

Effective emission of photoelectrons from the photoelectron emitting member is insured by applying uv rays to the photoelectron emitting member in an electric field.

The choice of an appropriate method for forming an electric field depends on such factors as the shape of a charging section used, its construction, the area of its application and the effect (precision) desired.

The strength of electric field to be applied can be properly determined in consideration of such factors as the concentration of concomitant water and the type of photoelectron emitting member used, the detailed information can be found in the specification of another commonly assigned invention. As a guide, an electric field having an intensity of from about 0.1 volt/cm to about 2 kilovolts/cm may be applied.

Electrodes that are used in applying an electric field may be made of any material in any construction commonly employed in ordinary charging devices. For instance, tungsten wires or rods may be used as electrodes.

The second aspect of the present invention which relates to a method of electrically charging fine particles using the photoelectron emitting member described above can be extensively used for the purpose of electrically charging flowing gas particles or the particles present in a confined space (stationary space). The method can be applied to any fields that utilize electrically charged particles for such purposes as modifying the surfaces of fine particles, controlling the quantity of electric charges on them, separating and classifying fine particles, measuring the concentration and size of fine particles in a space, as well as trapping and removing fine particles in a space to obtain clean gases. The term "space" as used herein includes a gas-containing space.

In the case of using the method of the present invention for producing clean gases, fine particles may be trapped by any means having the ability to trap charge fine particles. Common examples are the dust collecting plates (dust collecting electrodes) in ordinary charging devices, as well as electrostatic filters. Trapping means having a wooly structure in which the trapping section itself is composed of electrodes such as steel wool electrodes are also effective. If desired, electret members can also be used advantageously.

Also effective are the trapping methods that use ion-exchange filters (or fibers) as trapping media and that have already been proposed by the present inventor (see Japanese Patent Public Disclosure (Laid-Open) Nos. 54959/1988, 77557/1988 and 84656/1988). Ion-exchange filters are preferred for use in practical applications, since they are capable of trapping not only charged fine particles but also acidic gases, alkaline gases, odorous gases and other concomitant gases. The types of anion-exchange filters and cation-exchange filters, the amounts in which they are used and their relative proportions may be appropriately determined in accordance with various factors such as the polarity with which fine particles in gases are electrically charged, their concentrations, or the types of concomitant acidic, alkaline or adorous gases and their concentrations. For example, anion-exchange filters are effective for trapping negatively charged fine particles or acidic gases, whereas cation-exchange filters are effective for trapping positively charged fine particles or alkaline gases. In response to the concentrations of the materials to be trapped and their relative concentrations, the amounts in which those filters are to be used and their relative proportions may be properly determined in consideration of such factors as the field of application of equipment, its configuration, construction, operational efficiency and economy.

The photoelectron emitting member may be irradiated with sunlight that is directly applied to the glass material with which said member is combined. Alternatively, sunlight may be collected by an optical fiber through which it is guided to be applied to the photoelectron emitting member and this method will prove effective in some areas of application. Irradiation through optical fibers is effective in those areas of application where light transmissive materials cannot be used or for cleaning the air in spaces (e.g. underground spaces) where there is no exposure to direct sunlight.

It goes without saying that there is no need to use the light transmissive material when sunlight is to be irradiated through optical fibers since it can be directly applied to the photoelectron emitting member.

Any type of optical fiber can be used as long as sunlight can be guided to the photoelectron emitting member and a suitable optical fiber can be properly determined in consideration of such factors as the area of application, use conditions, the configuration of equipment, its size, the kind of photoelectron emitting member used, its shape, operational efficiency and economy. Quartz fibers are typically used with advantage.

EXAMPLES

The following examples are provided for the purpose of further illustrating the present invention but are in no way to be taken as limiting.

EXAMPLE 1

Figure 2:
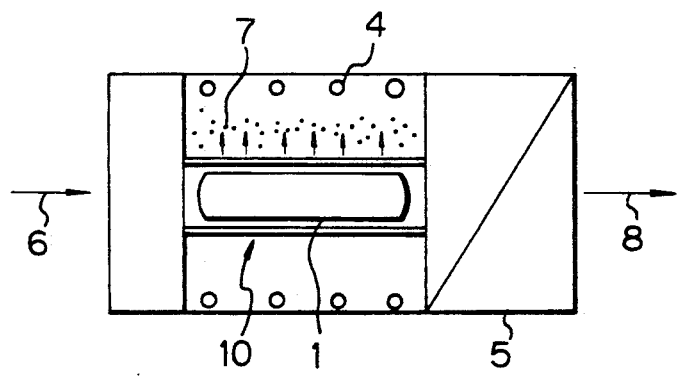
FIG. 2 is a schematic cross section of an air cleaner that uses the photoelectron emitting member of the present invention.
Figure 3:
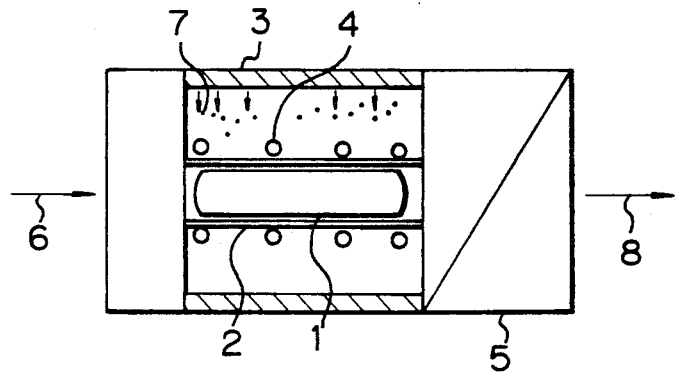
FIG. 3 is a schematic cross section of a prior art air cleaner.

FIG. 2 is a cross section showing an air cleaner that uses the photoelectron emitting member according to the first aspect of the present invention. As shown, the air cleaner is composed of an ultraviolet lamp 1, the photoelectron emitting member 10, electrodes 4 for establishing an electric field, and a charged fine particle trapping member 5.

Fine particles contained in an air 6 that is admitted into the air cleaner are electrically charged in an efficient manner with photoelectrons 7 that are emitted from the member 10 upon irradiation with ultraviolet rays from the lamp 1. The member 10 comprises a uv transmissive glass material and a thin gold film provided on its surface. The charged fine particles are trapped with the member 5 and clean air is obtained at an outlet 8.

Atmospheric air was supplied into the air cleaner of FIG. 2 at a flow rate of 3 l/min, with the cleaner being run continuously for a month. The fine particles in the air were electrically charged under the following conditions.

Photoelectron emitting member 10: synthetic quartz 3 mm thick provided with a thin Au film in a thickness of 50 Å;

UV lamp: germicidal lamp

Intensity of electric field created by electrodes 4: 50 V/cm.

A dust collecting plate was used as the charged fine particle trapping member 5. The concentration of the fine particles was measured with a particle counting apparatus.

The air was found to contain $1.2 \times 10^6$ particles (larger than 0.1 μm) per liter at inlet 6, and only 102 particles per liter at the outlet 8. The cleaner was continuously operated for a month and yet no change in its performance was found.

EXAMPLE 2

Figure 4:
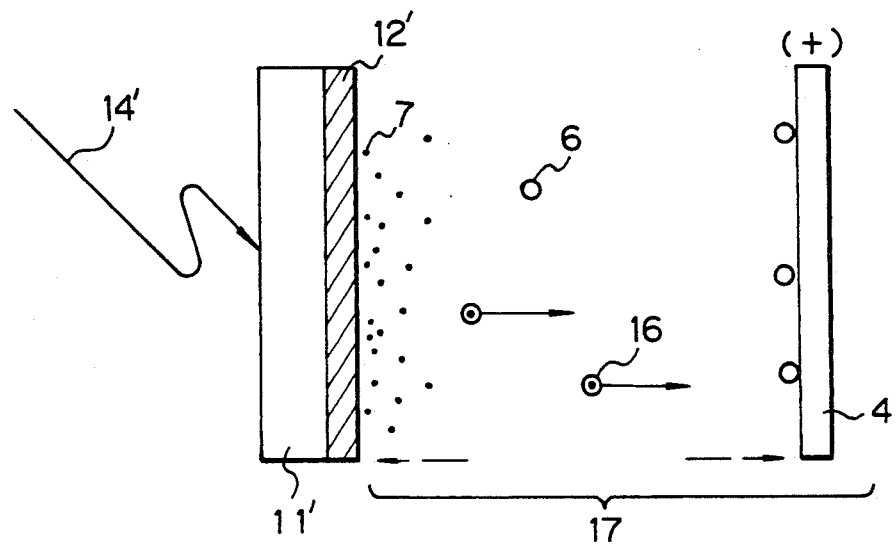
FIG. 4 is a schematic diagram showing the principle of trapping fine particles using sunlight as a source of uv rays in accordance with the present invention.

FIG. 4 is a schematic diagram showing the principle of trapping fine particles using sunlight as a source of uv rays in accordance with the present invention. Shown by 17 in FIG. 4 is a room containing air in which fine particles 6 of cigarette smoke and other particulate matters are suspended. The air is cleaned with sunlight 14' using an apparatus that comprises a glass substrate 11' and a trapping electrode 4. The glass substrate 11' is coated with a thin metal film 12', and the trapping electrode 4 also serves as an electrode for creating an electric field in which the fine particles are to be charged electrically.

Upon irradiation with sunlight, the thin metal film 12' on the glass substrate 11' emits photoelectrons 7 that charge the particles 6 electrically. The charged particles 16 are trapped by the electrode 4 positioned on one side of the room 17, whereby clean air is produced in the room. Convection promotes the cleaning process of air by its circulation. The thin metal film 12' is a photoelectron emitting material that emits photoelectrons upon irradiation with sunlight.

The apparatus being discussed here is used to clean the air in the passenger compartment of an automobile, with a thin gold film being coated on the window glass 11'. The trapping electrode 4 is made of a metal.

TEST

The apparatus shown in FIG. 4 was installed in an automobile and the concentration of fine particles in the air in the passenger compartment was measured with a particle counter. An electric field of 30 V/cm was created between the photoelectron emitting member (11'+12') and the electrode 4. The photoelectron emitting member was glass material 3 mm thick (synthetic quartz) having a Zr coat provided in a thickness of 50 Å.

RESULTS

The initial concentration of fine particles ($>0.1$ μm) which was $9.5 \times 10^6$ counts/cf dropped to $5.6 \times 10^5$ counts/cf after treatment under sunlight for 5 h.

EXAMPLE 3

Measurement of fine particles suspended in the air by the method of the present invention is specifically described with reference to FIG. 5.

Figure 5:
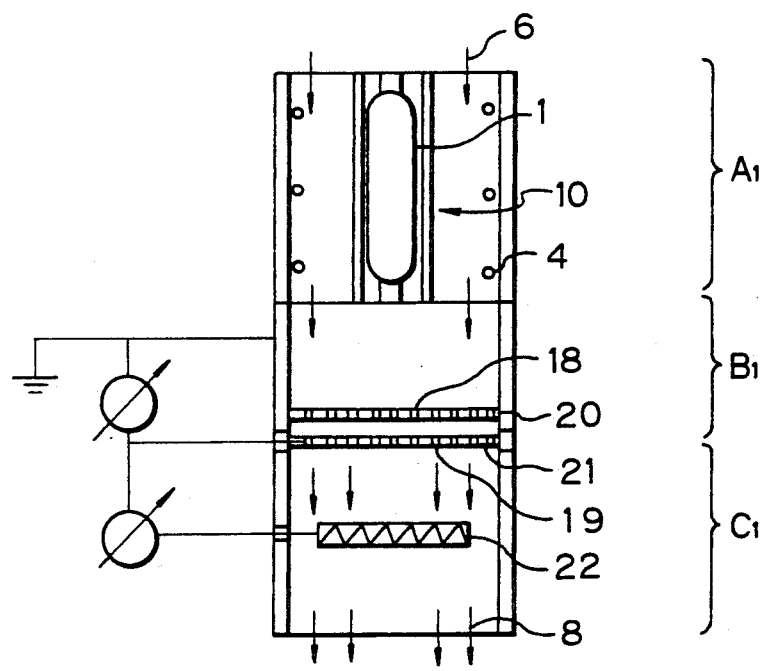
FIG. 5 is a schematic cross section of an apparatus used for measuring the fine particles suspended in air by the method of the present invention.

FIG. 5 shows schematically a measuring apparatus that uses classifying plates for classifying electrically charged fine particles and an electrometer as a detector. Air containing suspended fine particles 6 that is preliminarily cleaned of coarse particles larger than 10 μm by means of a suitable device such as an impactor (not shown) is introduced into the apparatus through an intake port. In a charging section $A_1$, the introduced fine particles are electrically charged with photoelectrons emitted from a photoelectron emitting member 10 upon irradiation with uv rays from a uv source 1.

The charging section $A_1$ is chiefly composed of the uv lamp 1, the photoelectron emitting member 10 and electrodes 4. In the charging section $A_1$, an electric field is formed between the photoelectron emitting member 10 and each of the electrodes 4 so that photoelectrons will be effectively emitted from the surface of the member 10 upon illumination with the uv lamp 1. The fine particles 6 in the air introduced through the intake port are electrically charged by the action of the emitted photoelectrons.

The charged fine particles are classified in a classifying section $B_1$.

The classifying section $B_1$ has a compact and simple construction for classifying the charged fine particles and performs the function of classifying them in response to the voltage applied to the classifying plates.

The operation of the classifying plates having pores 18 and 19 is described below.

An electric field as produced from a power source is formed between two classifying plates 20 and 21. Let the total number of charged fine particles in the classifying section $B_1$ be written as $b_1$. First, a weak electric field $a_1$ is formed between the plates 20 and 21, whereupon the charged particles $b_2$ that are small enough to be subjected to the action of the weak electric field are trapped on the classifying plates. As a result, the charge $d_1$ acting on the remaining coarse particles ($b_1-b_2$) is measured in a detecting section $C_1$ composed of an electrometer 22 positioned downstream of the classifying plates, whereby the concentration of the coarse particles is determined.

In the next place, an electric field $a_2$ stronger than $a_1$ is formed between the classifying plates 20 and 21, whereupon the charged particles $b_3$ that are coarser than $b_2$ are subjected to the action of that strong field and are trapped on the classifying plates. As a result, the charge level of the remaining coarse particles ($b_1-b_3$) is measured with the electrometer 22. In subsequent steps, the electric field applied to the classifying plates is properly changed to perform similar measurements of the electric charges on the charged particles.

Thus, the step of classification as combined with the measurement of the concentration of fine particles will provide information on the particle size distribution of the fine particles suspended in the air $I_2$ at the intake port, as well as the concentrations of the particles in respective size ranges.

In section $C_1$, the charged fine particles classified in the classifying section $B_1$ are detected with the electrometer 22.

The electrometer 22 may be of any type that is capable of measuring the charge level of the classified particles to provide information on the concentration of classified particles. Shown by 8 is an air outlet.

TEST

Using the apparatus shown in FIG. 5, the number of fine particles suspended in the air in a room was measured and the result was compared with the data obtained with a commercial electrical aerosol analyzer (EAA). The photoelectron emitting member 10 was a glass material 3 mm thick (synthetic quartz) coated with a thin Au film in a thickness of 50 Å. A germicidal lamp was used as the uv light source. An electric field having an intensity of 50 V/cm was created between the photoelectron emitting member 10 and the electrode 4. Air was supplied at the inlet at a flow rate of 0.5 l/min.

RESULTS

| Particle size | Count by the method (particles/cf) | Count by EAA (particles/cf) |
| --- | --- | --- |
| ≧0.05 μm | $8.24 \times 10^7$ | $8.65 \times 10^7$ |
| ≧0.1 μm | $1.85 \times 10^7$ | $1.92 \times 10^7$ |
| ≧0.3 μm | $1.25 \times 10^6$ | $1.31 \times 10^6$ |
| ≧2.0 μm | $1.2 \times 10^3$ | $1.25 \times 10^3$ |

EXAMPLE 4

An embodiment of the present invention which is directed to the classification of fine particles is described below with reference to FIG. 6.

Figure 6:
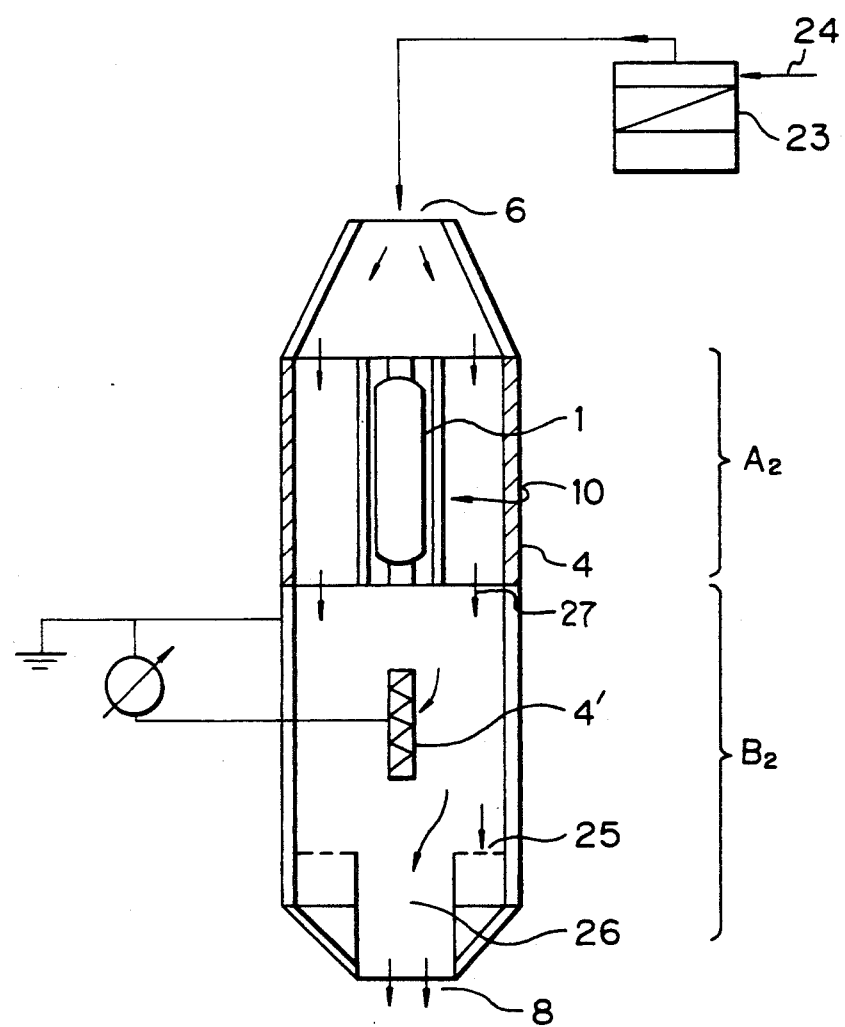
FIG. 6 is a schematic cross section of an apparatus for classifying fine particles by the method of the present invention.

FIG. 6 is a schematic cross section of an apparatus for classifying fine particles by the method of the present invention using ultraviolet rays. Shown by $A_2$ in FIG. 6 is a charging section in which the fine particles 6 in a gas stream introduced through an inlet 4 are electrically charged, and $B_2$ is a classifying section in which the charged particles are classified.

The fine particles to be introduced are preliminarily mixed under agitation in a mixing conditioner 23. When air 24 is introduced into the conditioner 23, it is freed of particles larger than 1 μm by a suitable means such as an impactor (not shown) before it is supplied into the charging section $A_2$.

The fine particles in the supplied air are electrically charged in the charging section $A_2$ with photoelectrons emitted from a photoelectron emitting member 10 upon irradiation with uv rays from a uv source 1. In the section $A_2$, the fine particles are efficiently charged and, if appropriate charging conditions are selected, the particles can be provided mostly with monovalent charges.

The charging section $A_2$ is chiefly composed of the uv generating source 1, the photoelectron emitting member 10 and an electrode 4. In the case under consideration, an electric field is created between the photoelectron emitting member 10 and the electrode 4.

The charged fine particles are classified in the section $B_2$ and a gas consisting of uniformly sized fine particles is obtained at an outlet 8. In the charging section $A_2$, the fine particles were efficiently electrified, mostly with monovalent charges, so uniformly sized fine particles can be efficiently obtained in the classifying section $B_2$ with suitably arranged electrodes in a suitably selected electric field.

The classifying section $B_2$ is composed of a trapping electrode 4' that is chiefly intended to trap and remove unwanted superfine particles, a screen 25 for removing relatively large particles (a weak electric field is applied to this screen and unwanted large particles are removed by drawing in the gas at a given flow rate), and a recovery port 26 for uniformly sized fine particles.

The group of fine particles that were electrically charged in section $A_2$ and that had a broad size distribution were first freed of unwanted superfine particles at the trapping electrode 4' and then freed of unwanted relatively large particles through the screen 25 under constant suction, whereupon the uniformly sized fine particles collected at the recovery port 26 and were then discharged through the outlet 8.

TEST

The apparatus shown in FIG. 6 was supplied with PSL (polystyrene latex) particles having a broad size distribution and the PSL particles were classified to obtain mono-dispersed particles. The photoelectron emitting member 10 was composed of a glass material 3 mm thick (synthetic quartz) coated with a thin Au film in a thickness of 40 Å. A germicidal lamp was used as the uv light source. An electric field having an intensity of 50 V/cm was created between the photoelectron emitting member 10 and the electrode 4. The PSL feed comprised particles having an average size (x) of 0.83 μm with a standard deviation (δ) of 0.95 μm. Hence, the coefficient of variation $$\left( CV = \frac{\delta}{x} \times 100 \right)$$

was 114.5%. A gas stream containing such PSL particles was introduced at a flow rate of 1.0 l/min.

RESULTS

The PSL particles recovered from outlet 8 had an average size of 0.83 μm, a standard deviation of 0.0080 μm, and CV value of 0.96%.

The PSL particles obtained at the outlet 27 of the charging section $A_2$ were introduced into a mobility analyzer to check the state and polarity of their electric charges. At least 95% of those particles were found to be negatively charged with a valence "1". In other words, the PSL feed that was a mixture of polyvalently charged particles and electrically neutral particles could be modified to negatively and monovalently charge fine particles by the method of the present invention.

ADVANTAGES OF THE INVENTION

The photoeletron emitting member of the present invention comprises a matrix capable of transmitting ultraviolet rays or sunlight and a material that is provided on the surface of the matrix or in its neighborhood and that emits photoelectrons upon irradiation with uv rays. Because of this arrangement, the present invention offers the following advantages:

(1) the photoelectron emitting member can be positioned so close (adjacent) to the source of uv radiation that the effect (performance) of photoelectron emission is enhanced;

(2) when sunlight is applied to the photoelectron emitting member to have the latter emit photoelectrones, particles can be electrically charged with the electrical cost being reduced to substantially zero;

(3) the enhanced and consistent emission of photoelectrons leads to effective electrical charging of fine particles (i.e., efficient charging can be performed for a prolonged period);

(4) the effective electrical charging of fine particles enables the use of a small (compact) apparatus and contributes to a larger throughput in processing, with the added advantage of a greater degree of freedom in the design of equipment; and (5) the fine particles in the system are not directly illuminated with uv rays, so they acquire only negative charges due to photoelectrons and this increases the practical value of the present invention depending on the area of its application.

Because of the advantages described above, the following benefits are achieved in various fields of application:

(I) In measurement applications,
  a. the measurement precision is improved and consistent results are attained for a prolonged period;
  b. a particularly great improvement is achieved in the precise measurement of superfine (<0.1 μm) particles;
(II) In applications where clean gases or liquids are to be obtained,
  a. improved performance is attained for a prolonged period;
  b. the apparatus size is reduced and the throughput of processing is increased;
(III) In applications where particle separation, classification, surface modification or controlling the quantity of electric charges is to be performed,
  a. improved performance is attained for a prolonged period;
  b. the apparatus size is reduced and the throughput of processing is increased; and
  b. a particularly great improvement is achieved in the efficiency of processing superfine (<0.1 μm) particles.

What is claimed is:

1. A photoelectron emitting member comprising a matrix that is at least composed of a first material capable of transmitting ultraviolet rays and a second material that is provided on the surface of said matrix or in its close vicinity and which emits photoelectrons upon irradiation with ultraviolet rays, said member emitting photoelectrons upon irradiation with ultraviolet rays in an electric field from the side opposite to the irradiated side, said second material having a thickness of from about 5 to about 5,000 Å and said matrix having a thickness of from about 0.5–about 40 mm.

2. A photoelectron emitting member according to claim 1 wherein said first material capable of transmitting ultraviolet rays is a glass material.

3. A photoelectron emitting member according to claim 1 wherein said second material emitting photoelectrons upon irradiation with ultraviolet rays is made of a material having a small photoelectric work function.

4. A photoelectron emitting member according to claim 1 wherein said second material emitting photoelectrons upon irradiation with ultraviolet rays is at least one material selected from the group consisting of Ba, Sr, Ca, Y, Gd, La, Ce, Nd, Th, Pr, Be, Zr, Fe, Ni, Zn, Cu, Ag, Pt, Cd, Pb, Al, C, Mg, Au, In, Bi, Nb, Si, Ta, Ti, U, B, Eu, Sn, P and compounds thereof.

5. A photoelectron emitting member according to claim 1 wherein said second material emitting photoelectrons upon irradiation with ultraviolet rays is an alloy, mixture or composite of at least two members selected from the group consisting of Ba, Sr, Ca, Y, Gd, La, Ce, Nd, Th, Pr, Be, Zr, Fe, Ni, Zn, Cu, Ag, Pt, Cd, Pb, Al, C, Mg, Au, In, Bi, Nb, Si, Ta, Ti, U, B, Eu, Sn, P and compounds thereof.

6. A method of electrically charging fine particles with photoelectrons comprising:
  providing a photoelectron emitting member including a matrix that is at least composed of a first material capable of transmitting ultraviolet rays and a second material that is provided on the surface of said matrix or in its close vicinity and which emits photoelectrons upon irradiation with ultraviolet rays, said member emitting photoelectrons upon irradiation with ultraviolet rays in an electric field from the side opposite to the irradiated side, said second material having a thickness of from about 5 to 5,000 Å and said matrix having a thickness of from about 0.5–about 40 mm; and
  irradiating the photoelectron emitting member with ultraviolet rays in an electric field having an intensity of from about 0.1 volt/cm to about 2 kilovolts/cm from the side opposite to the irradiated side.

7. A method of modifying the surfaces of fine particles and controlling the quantity of electric charges by utilizing the method of claim 6.

8. A method of separating and classifying fine particles by utilizing the method of claim 6.

9. A method of measuring the concentration and size of fine particles in a gas or a space by utilizing the method of claim 6.

10. A method of trapping and removing fine particles in a gas or space to produce a clean gas or space by utilizing the method of claim 6.

11. A method according to claim 6 wherein sunlight is used as a source of ultraviolet rays.

12. A method of modifying the surfaces of fine particles and controlling the quantity of electric charges by utilizing the method of claim 11.

13. A method of separating and classifying fine particles by utilizing the method of claim 11.

14. A method of measuring the concentration and size of fine particles in a gas or a space by utilizing the method of claim 11.

15. A method of trapping and removing fine particles in a gas or space to produce a clean gas or space by utilizing the method of claim 11.

* * * * *